United States Patent
Hoic et al.

(10) Patent No.: US 6,254,857 B1
(45) Date of Patent: Jul. 3, 2001

(54) EFFERVESCENT WHITENING DENTIFRICE HAVING OXYGEN-DERIVED SENSORY SIGNAL

(75) Inventors: Diego A. Hoic, Highland Park; David B. Viscio, Monmouth Junction; James G. Masters, Ringoes, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/577,439

(22) Filed: May 24, 2000

(51) Int. Cl.$^7$ ............... A61K 7/16; A61K 7/20
(52) U.S. Cl. .................. 424/53; 424/49
(58) Field of Search ........................... 424/49–88

(56) References Cited

FOREIGN PATENT DOCUMENTS

332551 * 9/1989 (EP).

* cited by examiner

Primary Examiner—Shep K. Rose
(74) Attorney, Agent, or Firm—Paul Shapiro

(57) ABSTRACT

An effervescent two component whitening dentifrice composition is disclosed which comprises a first component containing a peroxide compound such as hydrogen peroxide and a second dentifrice component containing a mixture of iron and copper salts such as $FeSO_4$ and $CaSO_4$, which when the two components are combined and mixed upon application to the teeth provides an effervescent sensory signal concomitant with whitening of the teeth.

12 Claims, No Drawings

EFFERVESCENT WHITENING DENTIFRICE HAVING OXYGEN-DERIVED SENSORY SIGNAL

BACKGROUND OF THE INVENTION

1. Field of the Invention

This invention relates generally to a two component effervescent dentifrice wherein, upon mixing of the separate components during brushing, significantly enhanced consumer perceived sensory sensations are provided which instill the consumer a perception of enhanced cleaning performance, and more particularly to a two component peroxide containing oral composition that provides enhanced sensory cues as well as providing a tooth whitening benefit.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate in the protein pellicle enamel layer of the tooth. These staining and discoloring substances can then permeate the enamel layer. This problem occurs gradually over many years, but imparts a noticeable discoloration of the enamel of one's teeth.

There are available in the marketplace oral compositions for home use which contain 1–3% by weight concentrations of a peroxide compounds such as hydrogen peroxide and when applied on the teeth effect whitening.

Illustrative of oral compositions containing peroxygen compounds for whitening teeth include U.S. Pat. Nos. 5,766,574 and 5,648,064.

U.S. Pat. No. 5,766,574 discloses dual component whitening dentifrice which comprises a first dentifrice component containing a peroxide compound such as urea peroxide and a second dentifrice component containing an abrasive such as alumina or silica which is incompatible with the peroxide, the first and second dentifrice components being maintained separate from the other until dispensed and combined for application to teeth requiring whitening.

U.S. Pat. No. 5,648,064 discloses a two component whitening dentifrice composition which discloses a first component containing a peroxygen compound such as hydrogen peroxide and a second dentifrice component containing a manganese coordination complex compound such as manganese gluconate, which activates the peroxygen compound and accelerates the release of active oxygen for rapid whitening action, the first and second components being maintained separate from the other until dispensed for application to teeth.

Further, it is known that bicarbonate-acid mixtures in toothpaste compositions will create an effervescent effect and that such effervescent effect can provide certain sensory and tooth cleaning benefits. For example, U.S. Pat. No. 5,885,871 discloses a two component effervescent dentifrice composition wherein the effervescent signal produced by the dentifrice derives form the evolution of carbon dioxide upon the mixing of a high alkaline pH paste (pH range 8–9) and a low acid pH (pH 2–4) gel.

There is an ongoing need for new and novel sensory benefits to promote the use of dentifrices and particularly in dentifrices used in the tooth whitening.

SUMMARY OF THE INVENTION

In accordance with the present invention there is provided, an effervescent peroxide containing oral composition for whitening of teeth wherein there is provided a two component composition of separate unmixed phases comprised of (a) a first component containing a water soluble peroxide compound contained in an orally acceptable vehicle and unmixed (b) a second component containing a mixture of iron and copper salts in an orally acceptable vehicle in an amount effective to activate the peroxide compound and accelerate the release of active oxygen, the two phases being combined shortly before application to the teeth wherein the iron and copper salts interact with the peroxide constituent to accelerate the breakdown and rapid release of active oxygen from the peroxide compound, such rapid release being effective for whitening teeth and instilling in the consumer a perception of enhanced product performance.

DETAILED DESCRIPTION OF THE INVENTION

In the practice of the present invention the first peroxide containing dentifrice component is a gel containing the peroxide ingredient and is formulated using a vehicle containing water, humectant, a peroxide compound as the whitening agent and a thickener such as a polyoxyethylene/polyoxypropylene block copolymer.

The amount of peroxide compound incorporated in the first gel component of the two component oral composition of the present invention will vary dependent upon its intended use. For use by trained professionals in office treatments, the concentration of peroxygen compound incorporated in the oral composition can vary from about 5 to about 30% by weight. For home use, such high concentrations of peroxide compounds cannot be used safely by the typical consumer and therefore the useful range of peroxide compound when the oral composition is a paste, gel or rinse is between 0.1 to 6.0% by weight. The preferred range is between about 0.5 to about 2.0% by weight.

Glycerin, and polyethylene glycol in combination with water are useful in formulating the vehicle for the whitening component of the dentifrice composition of the present invention. A combination of glycerine, polyethylene glycol and water is preferred as the vehicle in which the other ingredients of the peroxide component are contained.

Illustrative of polyethylene glycols useful in the practice of the present invention include polyethylene glycols known by the trademark Carbowax which are nonionic polymers of ethylene oxide having the general formula:

wherein n represents the average number of oxyethylene groups. The Carbowax polyethylene glycols are designated by a number such as 400, 600, 800, etc. which represents the average molecular weight. The average molecular weight of the polyethylene glycols used in the practice of the present invention is about 200–2000, preferably 400–800 and most preferably 600 (PEG 600).

Glycerin and polyethylene glycol is included in the peroxide dentifrice component of the present invention in an amount of from about 20 to about 50% by weight and preferably about 30 to about 45% by weight. Water is incorporated in the peroxide whitening dentifrice compositions of the present invention at a concentration of about 20 to about 50 by weight of the composition and preferably about 25 to about 40% by weight.

Thickening or gelling agents used in the formulation of the peroxide whitening dentifrice component include polyoxyethylene/polyoxypropylene block copolymers. Illustrative of polyoxyethylene/polyoxypropylene block copolymers useful in the practice of the present invention include block copolymers having the formula

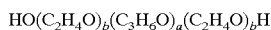

$$HO(C_2H_4O)_b(C_3H_6O)_a(C_2H_4O)_bH$$

wherein a is an integer such that the hydrophobic portion (moiety) represented by $(C_3H_6O)$ has a molecular weight of about 2750 to 4000, b is an integer such that the hydrophilic portion represented by $(C_2H_4O)$ constitutes about 70–80% by weight of the copolymer. Block copolymers of this composition are available commercially under the trademark Pluronic F type. Pluronic F127, which has a molecular weight of 4000 and contains 70% of the hydrophilic $C_2H_4O$ moiety is preferred in the practice of the present invention.

The thickening agent is preferably present in the peroxide dentifrice component in an amount within the range of about 10 to about 30% by weight and about 15 to 25% by weight is preferred.

The peroxide containing component is normally applied to the teeth in the form of an aqueous gel. The peroxide gel may be prepared by suspending the peroxide ingredient in the vehicle heated to a temperature of 45 to 140° C. by mixing in any suitable mixer, such as a Lightening mixer for about 30 minutes until a homogeneous solution is formed. A substantially rigid, non-fluid gel product is obtained upon cooling.

The dentifrice component in which an abrasive material is included is generally prepared using a vehicle which contains water, humectant, surfactant and thickener.

The humectant is generally a mixture of humectants, such as glycerin and sorbitol but other mixtures of humectants and single humectants may also be employed.

The humectant content is in the range of about 15% to about 30% by weight and preferably about 10 to about 20% by weight. The water content is in the range of about 10 to about 20% by weight.

The iron and copper salts respectively are present in the second component of the two phase whitening oral composition of the present invention at a weight ratio of 0.5:2.0 to 2.0 to 0.5 and preferably 1:1, such ratio being dependent upon the amount of peroxide compound incorporated in the first component. When the whitening oral composition is to be used by trained professionals and the first component contains relatively high concentrations of a peroxide compound, e.g., 5 to 35% by weight, the amount of iron and copper salts incorporated in the second component will range between about 1.0 to about 3% by weight and preferably between 1.5 to 2.0% by weight. For home use oral compositions in which the concentration range of peroxide compound in the first oral composition component is between about 0.1 to about 3.0% by weight, lower concentrations, e.g., between about 0.01 to about 1.0% by weight of iron and copper salt mixture is included in the second component and preferably about 0.03 to about 0.07% by weight.

To prepare the paste dentifrice component, polishing agents or abrasives are incorporated in the component and preferred polishing agents are siliceous materials, such as silica, which have a mean particle size up to about 20 microns. A preferred silica is a precipitated amorphous hydrated silica, such as that marketed under the trade designation Sylodent 783 XWA650 and Sylodent XWA 300 by W.R. Grace Company but other polishing agents may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina and bentonite.

The polishing agent is present in the paste component of the present invention at a concentration of about 10 to about 30% by weight and preferably 15 to about 25% by weight.

Inorganic thickeners may be included in the dentifrices of the present invention and include fumed silicas such as Cabosil available from Cabot Corporation, and thickening silicas including those available from J. M. Huber designated Zeodent 165.

Organic thickeners such as natural and synthetic gums and colloids may also be incorporated in the dentifrice compositions of the present invention. Examples of such thickeners include carrageenan (Irish moss), xanthan gum and sodium carboxymethyl cellulose, starch, polyvinylpyrrolidone, hydroxyethyl propylcellulose, hydroxybutyl methyl cellulose, hydroxypropyl methyl cellulose and hydroxyethyl cellulose and carboxyvinyl polymers such as Carbopol 934, 940, 941 available from B.F. Goodrich consisting of a collodially water soluble polymer of polyacrylic acid and cross-linked with from about 0.75% to about 2.0% of polyallyl sucrose or polyallyl pentaerythritol.

The inorganic or organic thickener may be incorporated in dentifrice components of the present invention at a concentration of about 0.05 to about 2% by weight and preferably about 0.1 to about 1.5% by weight.

Surface active agents are incorporated in the abrasive dentifrice component to provide foaming properties. The surface-active material is preferably anionic, nonionic or ampholytic in nature, and most preferably is anionic. Suitable examples of useful anionic surfactants are higher alkyl sulfates such as potassium or sodium lauryl sulfate which is preferred, higher fatty acid monoglyceride monosulfates, such as the salt of the monosulfated monoglyceride or hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine.

The surface active agent is generally present at a concentration of about 0.5 to about 5.0% by weight of the present invention in the abrasive dentifrice component.

Fluoride-providing salts having anti-caries efficacy may also be incorporated in the abrasive dentifrice component of the present invention and are characterized by their ability to release fluoride ions in water. Among these materials are inorganic metal salts, for example, sodium fluoride, potassium fluoride, a tin fluoride such as stannous fluoride or stannous chlorofluoride, sodium fluorosilicate, ammonium fluorosilicate and sodium monofluorophosphate. It is preferable to employ a fluoride salt to release about 10–1500 ppm of fluoride ion.

Synthetic anionic polymeric polycarboxylates optionally may be included in the abrasive dentifrice component. Polymeric polycarboxylates are well known, being often employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to 1,000,000. These copolymers are available for example as Gantrez AN 139 (M.W. 500,000), AN 119 (M.W. 250,000) and preferably S-97 Pharmaceutical Grade of ISP Corporation. Other operative polymeric polycarboxylates include those disclosed in U.S. Pat. No. 3,956,480, such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates include those disclosed in U.S. Pat. Nos. 4,138,477, and 4,183,914, such as copolymers of maleic anhydride with styrene, isobutylene or ethyl vinyl ether, polyacrylic, polyitaconic and polymaleic acids, and sulfoacrylic oligomers of molecular weight as low as 1,000, available as Uniroyal ND-2.

Other ingredients which may be incorporated in the abrasive dentifrice component of the present invention include pigment, sweetener, flavor and preservative. In white dental cream formulations, the pigment will be titanium dioxide, rutile, and the proportion thereof will normally be in the range of 0.5 to 1% by weight, preferably 0.75 to 1.25% by weight. The sweetener content will normally be that of an artificial or synthetic sweetener and the normal proportion thereof will be in the range of 0.1 to 1% by weight, preferably 0.3 to 0.5% by weight. The flavor content, which is preferably of a mixed peppermint/menthol flavor, will usually be in the range of 0.5 to 2% by weight, preferably 0.5 to 1.5% by weight. F.D. & C grade dyes may be used in appropriate amounts to provide desired colors.

Additional ingredients which may be incorporated in the abrasive dentifrice component of the present invention are antibacterial agents including noncationic antibacterial agents such as halogenated diphenyl ethers such as 2',4,4'-trichloro-2-hydroxy-diphenyl ether (Triclosan) and phenolic compounds including phenols, and their homologs, mono- and polyalkyl and aromatic halophenols, resorcinol and its derivatives, bisphenolic compounds and halogenated salicylanilides. Examples of other antibacterial agents which may be included in the abrasive dentifrice component include chlorhexidine, copper- and zinc-salts such as zinc citrate and sodium zinc citrate, sanguinarine extract, and metronidazole, quaternary ammonium compounds such as cetylpyridinium chloride, bis-guanides such as chlorhexidine digluconate, hexetidine, octenidine and alexidine.

The antibacterial agent is present in the abrasive dentifrice component in an effective antiplaque amount, typically 0.01–5% by weight, preferably about 0.03 to about 1% by weight.

Anti-inflammatory agents such as ibuprofen, flurbiprofen, aspirin, indomethacin etc. may also be included in the abrasive dentifrice component.

An anticalculus agent which is effective against calculus such as pyrophosphate salts including the mono, di, tri and tetra alkali metal and ammonium pyrophosphate and tripolyphosphate salts is still another additional ingredient which may be present in the abrasive component of the present invention . Such agents are used in amounts sufficient to reduce calculus and are preferably in amounts which will release about 1% by weight $P_2O_7$ ion and most preferably at least about 1.3% by weight $P_2O_7$ ion.

Salts having anti-tartar efficacy, including water soluble salts, such as dialkali or tetra-alkali metal pyrophosphate salts such as $Na_4P_2O_7$ (TSPP) $K_4P_2O_7$, $Na_2K_2P_2O_7$, $Na_2H_2P_2O_7$ and $K_2H_2P_2O_7$, long chain polyphosphate such as sodium hexametaphosphate and cyclic phosphates such as sodium trimetaphosphate as well as alkali metal tripolyphosphates such as sodium tripolyphosphate (STPP) and potassium tripolyphosphate may be incorporated in the dentifrice compositions of the present invention preferably at a concentration of about 0.5 to about 8.0% by weight.

A striped dentifrice product is obtained in accordance with the practice of the present invention wherein colorants of contrasting colors are incorporated in each of the dentifrice components used in the practice of the present invention, the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

The dyes used in the practice of the present invention are distributed uniformly throughout the dentifrice component and are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-N-ethyl-N-p-sulfobenzyl)-3,5-cyclohexadienimine], FD&C Blue No. 1 (disodium salt of dibenzyldiethyl-diaminotriphenylcarbinol trisulfonic acid anhydride), FD&C Blue No. 2 (sodium salt of disulfonic acid of indigotin) and mixtures thereof in various proportions. The concentration of the dye for the most effective result in the present invention is present in the dentifrice composition in an amount from about 0.0005 percent to about 2 percent by weight.

It is preferred that the colorant included in one of the dentifrice components be a pigment such as $TiO_2$ and that the colorant distributed throughout the vehicle of the other dentifrice component be a dye and that the dye be of a different color than the pigment included in the first dentifrice component. To avoid bleaching of the dye by the peroxygen compound constituent it is critical that the peroxygen compound not be included in the dentifrice component in which a peroxygen sensitive dye ingredient is included.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the oral composition components of this invention. Non-limiting examples thereof include preservatives, silicones and chlorophyll compounds, vitamins such as vitamins B6, B12, C, E and K, antibacterial agents such as chlorhexidene, halogenated diphenyl ethers such as triclosan, desensitizing agents such as potassium nitrate and potassium citrate and mixtures thereof. These adjuvants are incorporated in the oral composition components in amounts which do not substantially adversely affect the properties and characteristics desired, and are selected and used in proper amounts, depending upon the particular type of component involved.

To prepare the second abrasive dentifrice component of the present invention, the humectant and thickener are dispersed in a conventional mixer until the mixture becomes a slurry which is smooth in appearance, after which water is added. This mixture is heated to 100–100° F. and mixed for 10 to 30 minutes producing a homogeneous gel phase. Sweetener and color are added and mixed for 20 minutes. The mixture is transferred to a vacuum mixer and the abrasive is added and mixed for 10 to 30 minutes at high speed under a vacuum in the range of 5 to 100 millimeter of mercury pressure, preferably 5 to 50 mm Hg, providing a homogeneous mixture. The surfactant and flavor are then added to the paste which is followed by mixing another 10 to 20 minutes under vacuum of 5 to 50 mm Hg. The resultant product is an abrasive dentifrice paste of a texture like that of normal toothpastes having a pH in the range of 5 to 8, preferably 6.5 to 7.5, e.g., 7, and of satisfactory flavor.

Any convenient means for effecting the separation of the peroxide dentifrice component from the abrasive dentifrice component containing the accelerator mixture of iron and copper salts before being combined for use can be utilized. For example, a single container can be compartmentalized so that the peroxide containing dentifrice component and the abrasive containing component are housed in separate compartments and are not combined and admixed until extrusion from the dual compartment container and application to the teeth. Alternatively, the peroxide containing component and the abrasive containing component can be housed in separate containers from which the respective components are dispensed together and combined just prior to use.

The following examples are further illustrative of the present invention, but it is understood that the invention is not limited thereto. All amounts and proportions referred to herein and the appended claims are by weight.

EXAMPLE I

A peroxide gel and abrasive paste compositions useful as components of an effervescent dual component whitening dentifrice of the present invention were prepared with the following ingredients.

TABLE I

| Ingredients | Component A (Wt. %) | Component B (Wt. %) |
| --- | --- | --- |
| Dionized water | 13.91 | 29.497 |
| Glycerin | 12.00 | 30.00 |
| Sorbitol (70% solution) | 27.0 | 0.0 |
| Polyethylene glycol 600 | 0.00 | 10.00 |
| Na saccharin | 0.45 | 0.25 |
| Iota carrageenan | 0.35 | 0.00 |
| Carboxymethyl cellulose | 0.80 | 0.00 |
| NaF | 0.243 | 0.243 |
| Tetrasodium pyrophosphate (TSPP) | 1.00 | 0.00 |
| Sodium tripolyphosphate (STPP) | 7.00 | 0.00 |
| $TiO_2$ | 1.00 | 0.00 |
| FD&C - (1% solution) (Blue color) | 0.00 | 0.00 |
| Zeodent 165 | 1.50 | 0.00 |
| Sylodent 183 | 11.00 | 0.00 |
| Sylodent XWA 300 | 10.00 | 0.00 |
| Sodium lauryl sulfate | 1.50 | 0.00 |
| Hydrogen peroxide (35%) | 0.00 | 5.71 |
| $CaSO_4$ | 0.3285 | 0.00 |
| $FeSO_4$ | 0.3285 | 0.00 |
| NaOH | 2.00 | 0.00 |
| Flavor (Mint) | 1.90 | 0.30 |
| Gantrez S97 | 7.69 | 0.00 |
| Pluronic Fl27 | 0 | 21.00 |
| Phosphoric acid | 0 | 3.00 |
| Total | 100.00 | 100.00 |

Component A—Abrasive Paste Component

The glycerin, sorbitol, polyethylene glycol, carboxymethyl cellulose were dispersed in a conventional mixer until the mixture became a slurry, which was smooth in appearance, water was added and mixed for 10 to 30 minutes producing a homogeneous gel phase in which the sodium monofluorophosphate and Gantrez w as dispersed. Sweetener was added mixed for 20 minutes and transferred to a vacuum mixer. The alumina, silica and $TiO_2$ were then added and mixed for 10 to 30 minutes at high speed under a vacuum of about 50 mm Hg, providing a homogenous mixture. The sodium lauryl sulfate and flavor were then added to the paste which was followed by mixing another 20 minutes under vacuum of 50 mm Hg. The resultant product was a toothpaste with satisfactory flavor.

The Peroxide Gel Component

The peroxide dentifrice component was prepared in a Ross mixer. Water, NaF, saccharin, glycerin, phosphoric acid and PEG 600 were mixed for 10 minutes at low speed without vacuum. Pluronic F-127 was added and the mixture stirred for 30 minutes without vacuum and then an additional 30–45 minutes with vacuum of −15 mmHg. Then, peroxide was added with flavor and mixed for 10–15 minutes under vacuum. The resulting product was a gel.

To determine the level of oxygen generation obtained by combining Components A and B, equal amounts of paste Compositions A and the gel Composition B were combined and mixed in a beaker, the open end of which was then sealed with stretched parafilm. The evolution of oxygen gas could be observed within less than one minute after through mixingly which stretched the parafilm which swelled, as if it were a balloon being, inflated. Gas evaluation was also evident from the fact that the volume of the contents of the beaker increased significantly. For example 21.6% of the combined dentifrice components, occupying an initial volume of less than 10 ml, rose to significantly overflow a beaker with a 40 ml real total volume (30 ml nominal volume), in what corresponds to, at least, a 5-fold increase in volume.

A second formula contained the same ingredients, but with the following variations in their amounts: sorbitol, 27.607%; ferrous sulfate, 0.025%; cupric sulfate, 0.025%. This second batch showed that even when the total amount of metal salts was 0.05%, there was gas evolution. In contrast, a similar product in which the Fe and Cu salts were replaced with 0.05% manganese gluconate did not produce oxygen gas, even within 45 minutes.

EXAMPLE II

To test the whitening efficacy of dentifrice Components A and B, naturally stained human teeth were stained with a staining broth consisting of coffee, tea, mucin, microbiological media and a chromogenic microorganism. Stained teeth selected for the test showed the same amount of discoloration. To test the whitening efficacy of the combined components, the teeth were immersed in 2 grams of a mixture of equal amounts of Components A and B at 37° C. and then brushed 300 and 600 strokes. Before immersion, the color of the teeth was measured with a Minolta Chromameter in which L* is a measure of response to the eye to lightness and darkness, and b* is a measure of yellowness a* is a measure of blueness. The higher the L* value and lower b* value, the whiter teeth appear.

The whitening index was calculated using the following equation:

$$\Delta E = [(\Delta L^*)^2 + (\Delta a^*)^2 + (\Delta b^*)^2]^{1/2}$$

The higher the ΔE the greater the whitening effect observed.

The teeth remained immersed in the mixed components for 15 minutes. The whitening index (ΔE) of the immersed teeth is summarized in Table II below. The mixed components are designated Composition X in Table II.

For purposes of comparison, the procedure of Example II was repeated with exception that Component A did not contain the Fe/Cu salt mixture but was replaced with 0.05% manganese gluconate. This comparative composition was designated Composition "C". The whitening index of comparative Composition $C_1$ is also summarized in Table II below.

TABLE II

| Composition | ΔE<br>300 Strokes | ΔE<br>600 Strokes |
| --- | --- | --- |
| X | 2.81 ± 0.45 | 3.30 ± 1.26 |
| C | 2.23 ± 0.14 | 2.37 ± 0.13 |

What is claimed is:

1. A method of whitening stained or discolored teeth in the oral cavity with an enhanced sensory signal which comprises applying to the teeth a two component whitening composition, comprised of a first component containing in a vehicle a safe amount of a peroxide compound effective to whiten teeth, and a second component containing a mixture of iron and copper salts in a vehicle, the salt mixture being present in the vehicle in an amount effective to activate the peroxide compound, the first and second components being maintained separate from each other until dispensed for application to the teeth, dispensing and mixing the separately maintained components so that the iron and copper salt mixture of the second component interacts with the peroxide compound of the first component whereby the breakdown of the peroxide compound and the release of active oxygen provides effervescent sensory signal concomitant with whitening of the teeth.

2. The method of claim 1 wherein the peroxygen compound is hydrogen peroxide.

3. The method of claim 1 wherein the iron salt is a ferrous or ferric ion salt.

4. The method of claim 1 wherein the copper salt is a cupric ion salt.

5. The method of claim 1 wherein the iron salt is $FeSO_4$.

6. The method of claim 1 wherein the copper salt is $CuSO_4$.

7. A two component effervescent tooth whitening dentifrice composition which comprises a first dentifrice component containing a peroxide compound and a second dentifrice component containing a mixture of iron and copper salts, the first and second dentifrice components being maintained separate from each other until dispensed for application to teeth requiring the removal of stain and discoloration whereby the two components when combined and admixed during brushing provides an effervescent sensory signal concomitant with whitening of the teeth.

8. The composition of claim 7 wherein the peroxide compound is hydrogen peroxide.

9. The composition of claim 7 wherein the iron salt is a ferrous or ferric ion salt.

10. The composition of claim 7 wherein the copper salt is a cupric ion salt.

11. The composition of claim 7 wherein iron salt is $FeSO_4$.

12. The composition of claim 7 wherein the copper salt is $CuSO_4$.

* * * * *